US010160704B2

(12) United States Patent
Roesch et al.

(10) Patent No.: US 10,160,704 B2
(45) Date of Patent: Dec. 25, 2018

(54) METHOD AND APPARATUS FOR IMPROVING THE EFFICIENCY OF REFORMING PROCESS FOR PRODUCING SYNGAS AND METHANOL WHILE REDUCING THE CO2 IN A GASEOUS STREAM

(71) Applicant: L'Air Liquide, Société Anonyme pour l'Etude et l'Exploitation des Procédés Georges Claude, Paris (FR)

(72) Inventors: Alexander Roesch, Katy, TX (US); Alain Guillard, Houston, TX (US)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 0 days.

(21) Appl. No.: 15/630,301

(22) Filed: Jun. 22, 2017

(65) Prior Publication Data

US 2018/0258019 A1 Sep. 13, 2018

Related U.S. Application Data

(60) Provisional application No. 62/470,420, filed on Mar. 13, 2017.

(51) Int. Cl.
*C07C 31/04* (2006.01)
*C01B 3/48* (2006.01)
(Continued)

(52) U.S. Cl.
CPC ............ *C07C 29/1518* (2013.01); *C01B 3/34* (2013.01); *C01B 3/48* (2013.01); *C07C 31/04* (2013.01);
(Continued)

(58) Field of Classification Search
CPC ..... C01B 3/48; C01B 3/56; C01B 2203/0233; C01B 2203/0283; C01B 2203/042;
(Continued)

(56) References Cited

U.S. PATENT DOCUMENTS

| 4,181,675 A | 1/1980 | Makin et al. |
| 6,214,314 B1 * | 4/2001 | Abbott ................. C01B 3/38 |
| | | 423/650 |

(Continued)

FOREIGN PATENT DOCUMENTS

| DE | 20 24 301 | 12/1971 |
| GB | 1 309 872 | 3/1973 |
| WO | WO 2015 165818 | 11/2015 |

OTHER PUBLICATIONS

International Search Report and Written Opinion for corresponding PCT/US2018/022110, dated May 29, 2018.

*Primary Examiner* — Jafar F Parsa
(74) *Attorney, Agent, or Firm* — Elwood L. Haynes

(57) ABSTRACT

A method for the co-production of hydrogen and methanol including a hydrocarbon reforming or gasification device producing a syngas stream comprising hydrogen, carbon monoxide and carbon dioxide; introducing the syngas stream to a water gas shift reaction thereby converting at least a portion of the CO and H2O into H2 and CO2 contained in a shifted gas stream; cooling the shifted gas stream and condensing and removing the condensed fraction of H2O; then dividing the shifted syngas stream into a first stream and a second stream; introducing the first stream into a first hydrogen separation device, thereby producing a hydrogen stream, and introducing the second stream into a methanol synthesis reactor, thereby producing a crude methanol stream and a methanol synthesis off gas; introduc- (Continued)

ing at least a portion of the methanol synthesis off gas into a second hydrogen separation device.

20 Claims, 5 Drawing Sheets

(51) Int. Cl.
*C01B 3/34* (2006.01)
*C07C 29/151* (2006.01)
(52) U.S. Cl.
CPC ............. *C01B 2203/0205* (2013.01); *C01B 2203/0283* (2013.01); *C01B 2203/061* (2013.01); *C01B 2203/062* (2013.01)
(58) Field of Classification Search
CPC ...... C01B 2203/043; C01B 2203/0475; C01B 2203/061; C01B 2203/0827; C01B 2203/1241; C01B 2203/148; C07C 31/04; C07C 29/1518
See application file for complete search history.

(56) References Cited

U.S. PATENT DOCUMENTS

| | | | |
|---|---|---|---|
| 6,706,770 B2 | 3/2004 | Patel et al. | |
| 2003/0191196 A1 | 10/2003 | Madhubhai et al. | |

\* cited by examiner

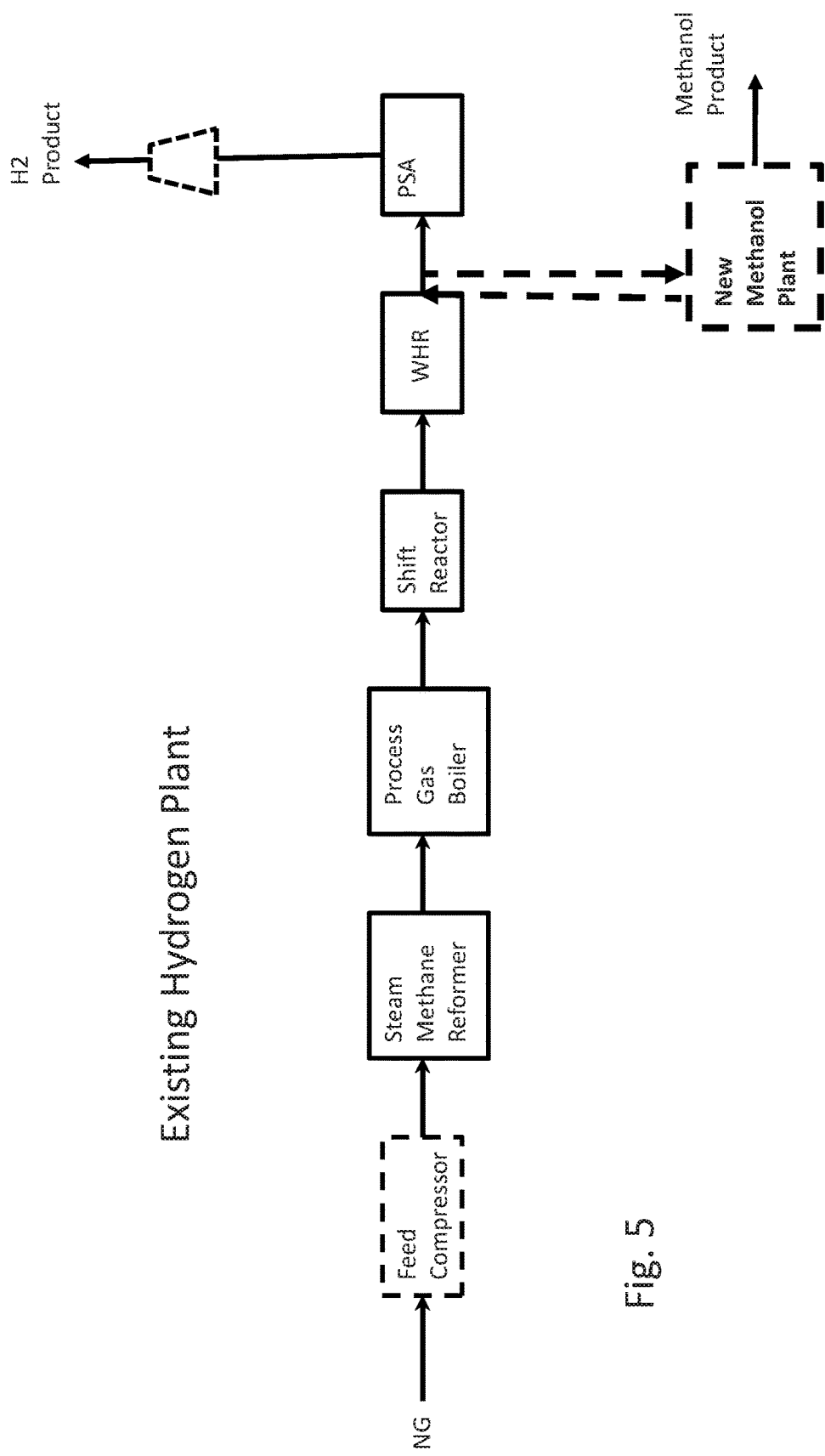

METHOD AND APPARATUS FOR IMPROVING THE EFFICIENCY OF REFORMING PROCESS FOR PRODUCING SYNGAS AND METHANOL WHILE REDUCING THE CO2 IN A GASEOUS STREAM

BACKGROUND

A significant portion of the world's methanol is produced by the catalytic reaction of synthesis gas obtained by reforming hydrocarbons. The synthesis gas may be produced in a steam reformer, an autothermal reformer, or a partial oxidation reformer containing hydrogen, carbon monoxide, and carbon dioxide.

The majority of hydrogen is produced from a synthesis gas produced by the mentioned reforming technologies. For hydrogen production the hydrogen content in the syngas shad be as high as possible whereas for methanol production a suitable synthesis gas composition may be characterized by a hydrogen-carbon oxide molar ratio defined as:

$$\frac{[H_2] - [CO_2]}{[CO] + [CO_2]}$$

where $[H_2]$, $[CO]$, and $[CO_2]$ are the mole fractions of the respective components in the synthesis gas.

Hydrogen Production

FIG. 1 illustrates a typical synthesis gas (syngas) plant for hydrogen production as known to the art. A light hydrocarbon, natural gas in this example, is fed into a reformer. A steam methane reformer is indicated in FIG. 1, but the above discussed processes apply equally well, depending on the type of feedstock, desired ratio of carbon monoxide, carbon dioxide and hydrogen. Depending on the available natural gas supply pressure, a feed compressor may be needed. As the syngas is generated at a very high temperature, this gas stream may be cooled in a process gas boiler, thereby producing steam which may be useful elsewhere and thus improving the thermal efficiency of the facility.

If additional hydrogen is desired, a water gas shift reactor may be utilized. Any additional useful heat in the shifted syngas stream may then be extracted in a syngas waste heat recovery unit. As high purity hydrogen is often the desired product from such a system, a hydrogen separation device, a pressure swing adsorption unit in FIG. 1, may be used to separate the hydrogen for export. Optionally, a portion of the purified hydrogen gas may be blended with the light hydrocarbon feed stream (i.e. natural gas) and fed into the reformer. If no feed compressor is present upstream of the reformer, a dedicated hydrogen recycle compressor may be required.

Methanol Production

Methanol may be formed from synthesis gas by the following reactions:

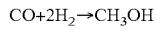

$$CO + 2H_2 \rightarrow CH_3OH$$

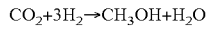

$$CO_2 + 3H_2 \rightarrow CH_3OH + H_2O$$

FIG. 2 illustrates a combined hydrogen and methanol production facility as known to the art (see U.S. Pat. No. 6,706,770 for example). A light hydrocarbon, natural gas in this example, is fed into a reformer. A steam methane reformer is indicated in FIG. 2, but the above discussed processes apply equally well, depending on the type of feedstock, desired ratio of carbon monoxide, carbon dioxide and hydrogen. Depending on the available natural gas supply pressure, a feed compressor may be needed. As the syngas is generated at a very high temperature, this gas stream may be cooled in a process gas boiler, thereby producing steam which may be useful elsewhere and thus improving the thermal efficiency of the facility.

In the process scheme of FIG. 2, the cooled syngas is split into a first stream that is combined with process steam and enters the shift reactor (as discussed above). Then into a waste heat recovery unit, and then a hydrogen separation device, such as a pressure swing adsorption unit, to produce hydrogen for downstream use. The cooled syngas is split into a second stream that enters a second waste heat recovery unit, then is compressed and then introduced into a methanol reactor, thus producing a crude methanol stream for use downstream.

In order to utilize the synthesis gas most efficiently in the above reactions, stoichiometric amounts of hydrogen and carbon oxides are preferred. Synthesis gas with a suitable stoichiometric composition for methanol production has a value of the hydrogen-carbon oxide molar ratio of 2.0-2.4. Methanol is produced by reacting the synthesis gas catalytically in a pressurized reactor to yield methanol and unreacted synthesis gas, the methanol is condensed and separated from the unreacted synthesis gas, and a portion of the unreacted synthesis gas is recycled to the reactor feed to increase overall conversion. A certain percentage of the unreacted synthesis gas must be purged from the methanol reactor loop so that components who may be present the synthesis gas but not participating in the methanol synthesis e.g. N2 and CH4, Ar do not build up in the reactor feed gas.

Synthesis gas produced by steam reforming of light hydrocarbons generally contains excess hydrogen when used for methanol production. Thus while purging inert components out of the methanol synthesis loop a significant amount of unreacted hydrogen must be withdraw and may be used as waste fuel. This purge gas also contains valuable carbon oxides, which become unavailable for conversion to methanol, and this loss adversely affects methanol production economics.

Several approaches to minimize the amount of purge gas or to valorize the purge gas differently have been utilized in commercial methanol production. In one approach, imported carbon dioxide is mixed with either the synthesis gas feed to the methanol reactor or the feed hydrocarbon to the steam reforming step. This gives a methanol reactor feed gas that is closer to the preferred stoichiometric composition, but is possible only when a source of carbon dioxide is readily available. In another approach, unreacted synthesis gas is separated by various methods into a stream enriched in carbon oxides and a stream enriched in hydrogen, the carbon oxide-rich stream is recycled to the reformer or the methanol reactor, and the hydrogen-enriched stream is used for fuel. Membrane systems, absorption processes, and pressure swing adsorption have been used to effect separation of the unreacted synthesis gas.

An alternative approach is to generate the synthesis gas by methods other than steam reforming wherein these methods produce a synthesis gas closer to the preferred hydrogen-carbon oxide ratio for methanol production. Known methods to generate the preferred synthesis gas composition include the partial oxidation, autothermal reforming, and a two-stage process comprising steam reforming followed by oxygen secondary reforming. These methods all require a supply of oxygen, however, and the capital costs are higher than for simple steam reforming.

In order to increase the production efficiency of hydrogen and methanol this invention provides a cost effective system for co-production of hydrogen and methanol. The instant process focuses on retrofitting an existing hydrogen plant and avoiding extra equipment and minimizing the impact on the existing hydrogen plant. But this process may be also applied to a new plant to co-produce hydrogen and methanol.

SUMMARY

A method for the co-production of hydrogen and methanol including a hydrocarbon reforming or gasification device producing a syngas stream comprising hydrogen, carbon monoxide and carbon dioxide; introducing the syngas stream to a water gas shift reaction thereby converting at least a portion of the CO and H2O into H2 and CO2 contained in a shifted gas stream; cooling the shifted gas stream and condensing and removing the condensed fraction of H2O, thus producing a dried, shifted syngas stream; dividing the dried, shifted syngas stream into a first stream and a second stream; introducing the first stream into a first hydrogen separation device, thereby producing a hydrogen stream, and introducing the second stream into a methanol synthesis reactor, thereby producing a crude methanol stream and a methanol synthesis off gas; introducing at least a portion of the methanol synthesis off gas into the first or separate second hydrogen separation device.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein:

FIG. 5 is a schematic representation fundamentally illustrating how the hydrogen plant of FIG. 1 may be retrofitted into the combined plants of FIG. 3 or 4.

DESCRIPTION OF PREFERRED EMBODIMENTS

Figure 1:
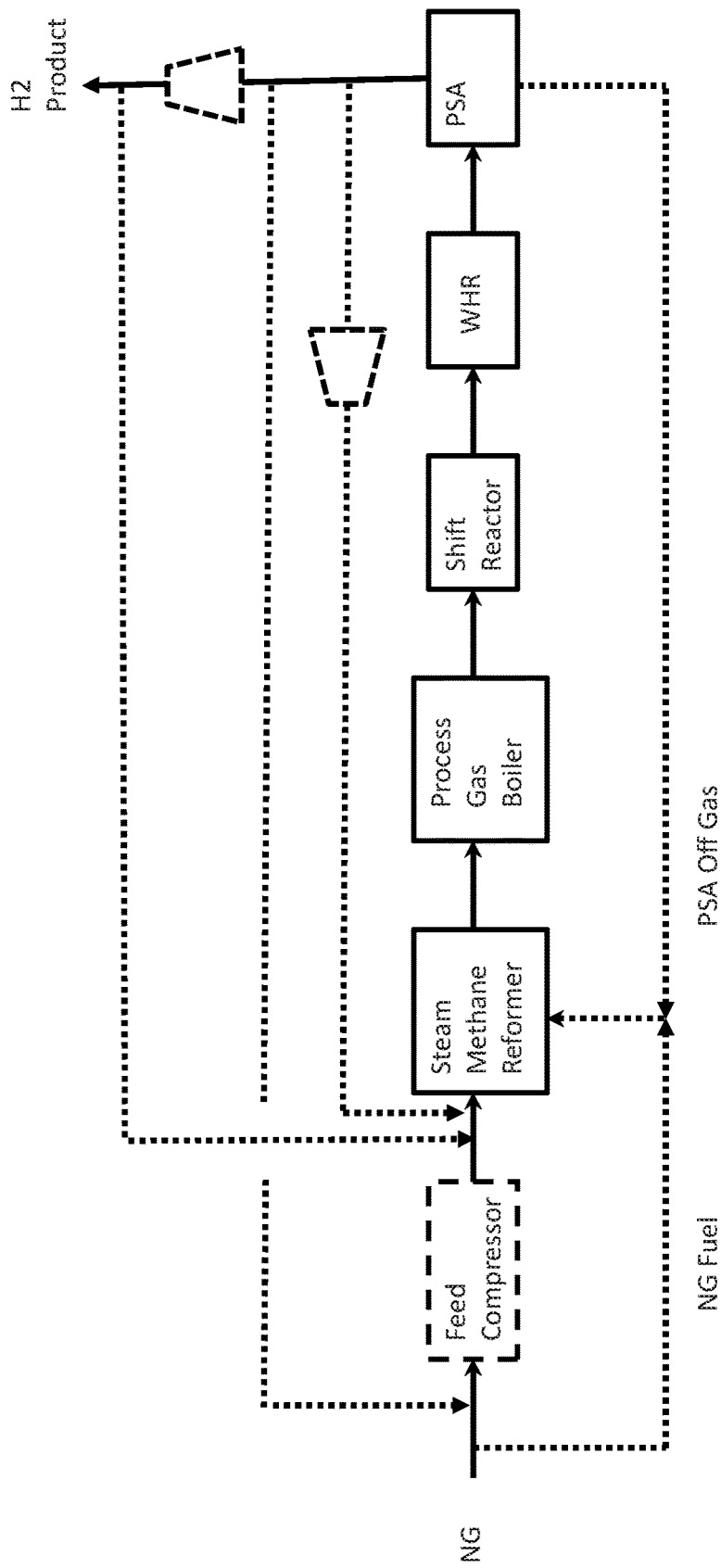
FIG. 1 is a schematic representation a typical steam methane reformer hydrogen plant, as is known to the art.
Figure 2:
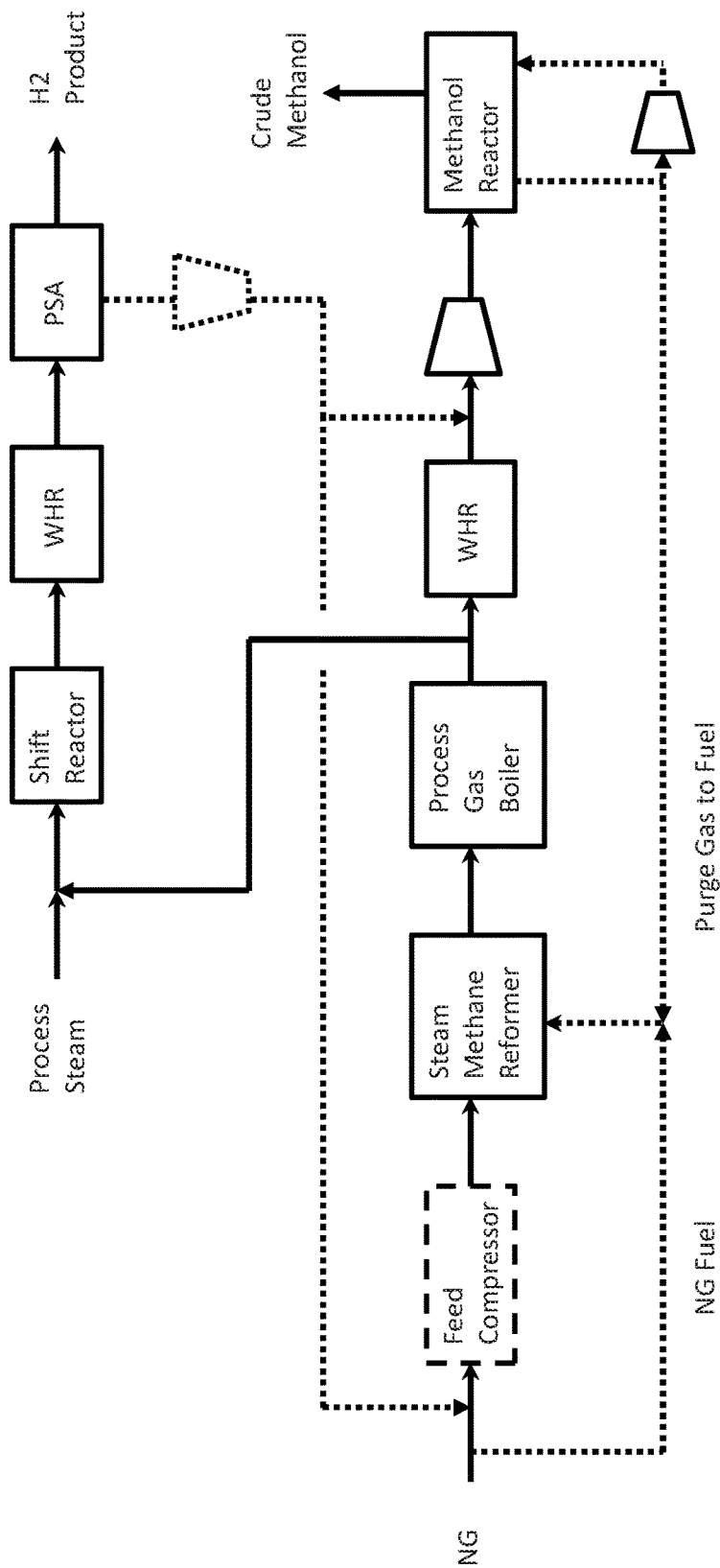
FIG. 2 is a schematic representation of a typical combination methanol and hydrogen plant, as is known to the art.

Element Numbers:
101=hydrocarbon feed stream
102=feed compressor
103=synthesis gas reactor/generator
104=process gas waste heat boiler
105=water gas shift reactor
106=waste heat recovery system
107=first hydrogen separation device
108=product hydrogen compressor
109=first product hydrogen stream
110=methanol loop reactor
111=methanol purification unit with distillation column
112=methanol synthesis off gas recycle compressor
113=methanol synthesis make-up gas compressor
114=purified methanol product stream
115=crude methanol product stream
116=steam export stream
117=unshifted syngas bypass stream (bypassing the water gas shift reactor)
118=process off-gas stream (to synthesis gas reactor as fuel or feed)
119=methanol distillation column off-gas stream
120=shifted syngas stream (input to methanol reactor) (Second Stream)
121=hydrocarbon feed to fuel (to reactor burners)
122=methanol synthesis off gas stream to hydrogen separation device
123=steam to methanol distillation column
124=crude methanol to methanol purification
125=hydrogen stream to hydrocarbon feed stream
126=shifted syngas stream to first hydrogen separation device (First Stream)
127=steam stream to synthesis gas reactor
128=first high purity hydrogen stream
129=methanol synthesis off gas stream to hydrocarbon feed stream
130=second hydrogen separation device
209=second product hydrogen stream
218=process off gas stream from second hydrogen separation device
225=high pressure hydrogen to the hydrocarbon feed stream
228=second high purity hydrogen stream Illustrative embodiments of the invention are described below. While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

As used herein, the term "methanol loop reactor" is defined as a high pressure reactor, typically requiring an inlet compressor, wherein the product stream exiting the reactor (crude methanol and unreacted syngas) is sent to a methanol separator, wherein a stream of crude methanol is removed from the cycle, and most of the remaining gas (minus a certain amount of purge gas which leaves the system) is recycled back to a recycle compressor and then is blended with the incoming syngas stream and returned to the methanol reactor.

This invention relates to a method for the co-production of methanol and hydrogen from synthesis gas obtained by reforming light hydrocarbons. As broadly illustrated in FIG. 5, in one embodiment, the current invention addresses revamping an existing hydrogen plant, with a focus on avoiding any unnecessary extra equipment and minimizing process impact on the existing hydrogen plant (for example fewer tie-in points) thus making retrofitting an existing plant easier and less expensive. In another embodiment, the present invention may be applied to a new plant to co-produce hydrogen and methanol. Another advantage of the instant process compared to the prior art is that it requires only a single waste heat recovery/cooling, thus requiring less capital expenditure is required.

Figure 3:
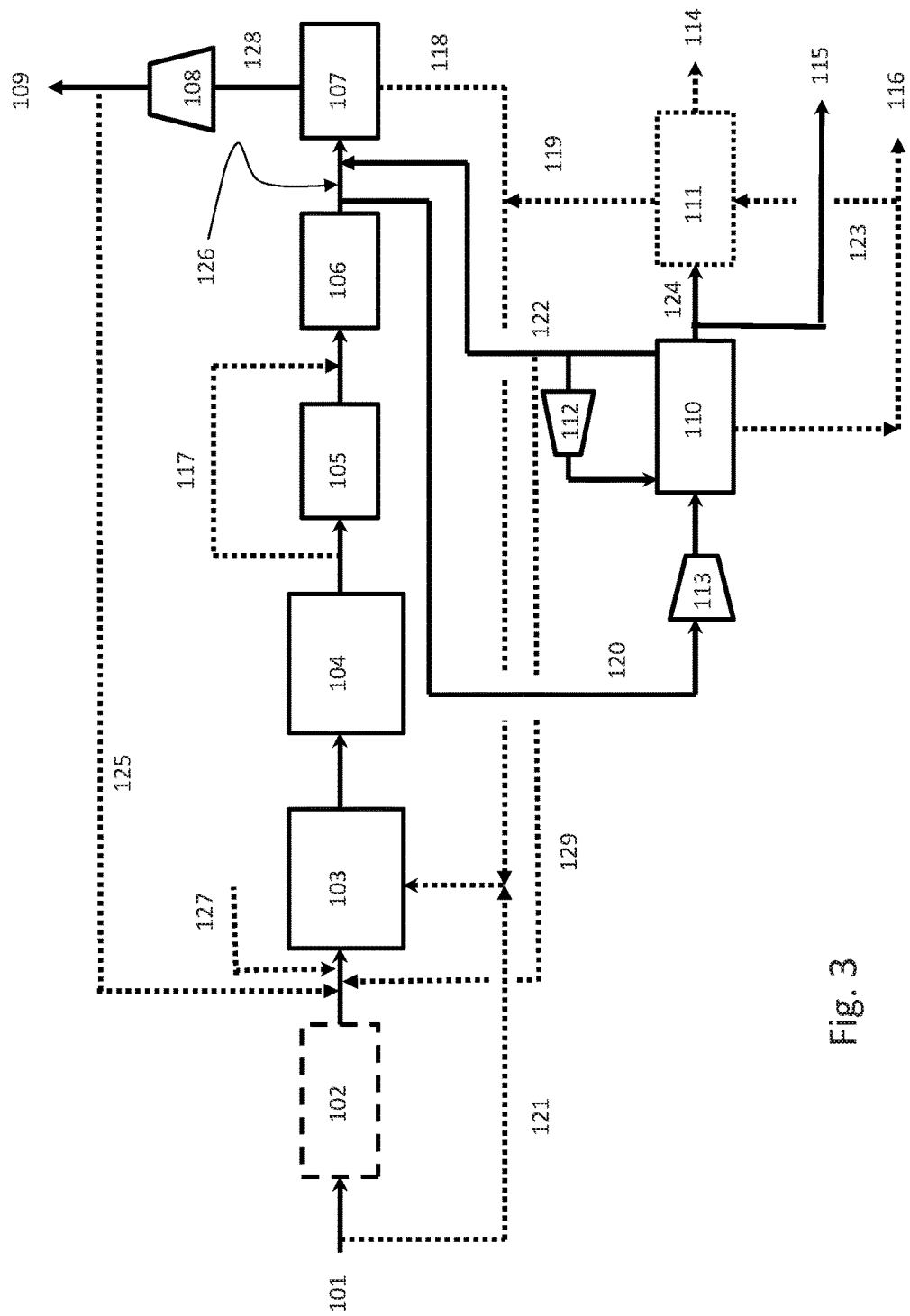
FIG. 3 is a schematic representation of a combination methanol and hydrogen plant, in accordance with one embodiment of the present invention.

Referring now to FIG. 3, one embodiment of the present invention is illustrated. A hydrocarbon feed stream 101 is introduced into synthesis gas (syngas) reactor 103 as process feed. The hydrocarbon process feed stream 101 may be natural gas. The syngas reactor 103 may be a steam methane reformer (SMR), an autothermal reformer (ATR), or a partial oxidation reformer (PDX) or a combination of any of the possible reactor systems. If necessary, hydrocarbon stream 101 may need an increase in downstream pressure, in which case feed compressor 102 may be required. Depending on the selected syngas reforming technology a portion of the hydrocarbon stream 121 may be fed into the synthesis gas reactor 103 as fuel. If necessary, steam stream 127 may be introduced into syngas reactor 103. Syngas reactor 103 thus produces a synthesis gas that contains hydrogen, CO, CO2 and other impurities.

The syngas that exits the syngas reactor 103 is typically between 1400° F. and 3000° F.; therefore, waste heat boiler 104 may be used to recover heat from the hot process gas. The cooled syngas is then introduced into water gas shift reactor 105 in order to convert some of the CO to hydrogen and CO2. An H2O stream might be introduced upstream the shift reactor 105, but is not shown. Shift reactor 105 may be a high temperature shift, a medium temperature shift, a low temperature shift or a combination. As used herein, the term "low temperature shift" refers to a water gas shift conversion reaction that operates at a temperature between about 350° F. and 500° F. As used herein, the term "medium temperature shift" refers to a water gas shift conversion reaction that operates at a temperature between about 400° F. and 675° F. As used herein, the term "high temperature shift" refers to a water gas shift conversion reaction that operates at a temperature between about 600° F. and 950° F. A bypass 117 around shift reactor 105 may be added to adjust the synthesis gas composition to a more suitable composition for producing methanol.

As any of these shift reactions take place at temperatures which would be harmful to most hydrogen separation systems, further cooling of the shifted syngas is required. The shifted syngas may enter additional steam boiler system, boiler feed water preheater or any other type of heat exchanger to recover the sensible heat from the shifted syngas. Prior to entering the purification unit a final cooling step using air cooler of cooling water cooler is typically foreseen. The described additional cooling section can vary depending on the overall plant heat integration and is represented by the unit 106. The cooled, shifted syngas stream is then split into two streams 126 and 120. Stream 126 is sent to first hydrogen separation device 107, wherein hydrogen stream 128 and PSA off gas stream 118 are produced. First hydrogen separation device 107 may be a pressure swing adsorption unit (PSA), or a membrane unit. If necessary, hydrogen stream 128 may be introduced into hydrogen compressor 108, thus producing compressed hydrogen stream 109.

Stream 120 is feed into shifted gas compressor 113, then into methanol reactor 110. The cooled, shifted synthesis gas typically enters the methanol synthesis loop 110 at a pressure of between about 60-120 bar. At least a portion of synthesis gas is converted to methanol in the methanol synthesis loop 110. The formed crude methanol is separated from the unreacted synthesis gas by means of a gas liquid separation device (not shown). The separated crude methanol may be sent out as a product 115 or sent to the methanol distillation 111 to make high purity methanol as a product 114. The off gas 119 from the distillation column 111 may also sent back to synthesis gas reactor 103 to be used as a fuel.

For the unreacted synthesis gas, at least a portion may be recycled back to the methanol loop, passing through methanol recycle compressor 112. Any remaining unreacted syngas 122 may be mixed with cooled shifted synthesis gas 126 and sent to first hydrogen separation device 107, thus producing high purity hydrogen product stream 128. A portion of the hydrogen product may be sent back to the hydrocarbon feed stream 129. The off gas 118 from the first hydrogen separation device 107 may be sent back to synthesis gas reactor 103 to be used as a fuel. The high purity hydrogen 128 may be compressed 108 and exported as a product hydrogen stream 109, a portion 125 of the hydrogen may be sent back to the hydrocarbon feed stream. A portion of this hydrogen may be used in a hydrodesulfurization (HDS) reactor (not shown) to remove sulfur from natural gas if necessary.

Figure 4:
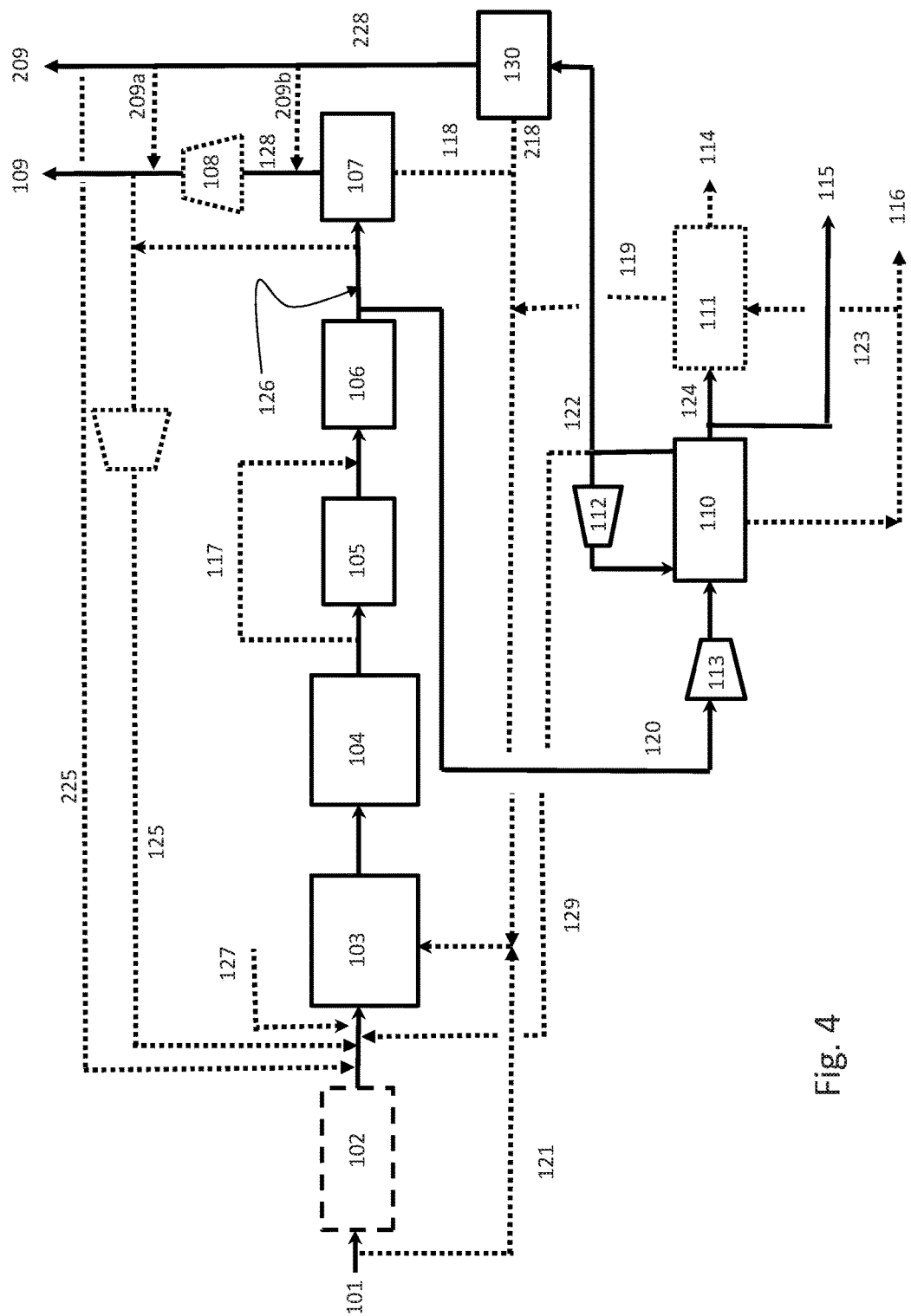
FIG. 4 is a schematic representation of a combination methanol and hydrogen plant, in accordance with another embodiment of the present invention.

Referring now to FIG. 4, another embodiment of the present invention is illustrated. A hydrocarbon feed stream 101 is introduced into syngas reactor 103. The hydrocarbon feed stream 101 may be natural gas. The syngas reactor 103 may be a steam methane reformer (SMR), an autothermal reformer (ATR), or a partial oxidation reformer (PDX) or a combination of any of the possible reactor systems. If necessary, hydrocarbon stream 101 may need an increase in downstream pressure, in which case feed compressor 102 may be required. If necessary, steam stream 127 may be introduced into syngas reactor 103. Syngas reactor 103 thus produces a synthesis gas that contains hydrogen, CO, CO2 and other impurities.

The syngas that exits the syngas reactor 103 is typically between 1400° F. and 3000° F.; therefore, waste heat boiler 104 may be used to recover heat from the hot process gas. The cooled syngas is then introduced into water gas shift reactor 105 in order to convert some of the CO to hydrogen and CO2. An H2O stream might be introduced upstream the shift reactor 105, but is not shown. Shift reactor 105 may be a high temperature shift, a medium temperature shift, a low temperature shift or a combination. As used herein, the term "low temperature shift" refers to a water gas shift conversion reaction that operates at a temperature between about 350° F. and 500° F. As used herein, the term "medium temperature shift" refers to a water gas shift conversion reaction that operates at a temperature between about 400° F. and 675° F. As used herein, the term "high temperature shift" refers to a water gas shift conversion reaction that operates at a temperature between about 600° F. and 950° F. A bypass 117 around shift reactor 105 may be added to adjust the synthesis gas composition to a more suitable composition for producing methanol.

As any of these shift reactions take place at temperatures which would be harmful to most hydrogen separation systems, further cooling of the shifted syngas is required. The shifted syngas may enter additional steam boiler system, boiler feed water preheater or any other type of heat exchanger to recover the sensible heat from the shifted syngas. Prior to entering the hydrogen separation device 107, 130, a final cooling step using air cooler of cooling water cooler is typically foreseen. The described additional cooling section can vary depending on the overall plant heat integration and is represented by the unit 106. The cooled, shifted syngas stream is then split into two streams 126 and 120. Stream 126 is sent to first hydrogen separation device 107, wherein hydrogen stream 128 and PSA off gas stream 118 are produced.

As used herein, the term "high pressure PSA" may be understood in the following context. An SMR typically operates at pressures of between 15 barg and 45 barg. A PDX typically operates at pressures of between 30 barg and 100 barg. An ATR typically operates at pressures of between 30 barg and 100 barg. A hydrogen PSA typically operates at pressures as high as 30 barg or 45 barg. Hence, as used herein, a "high pressure PSA" is one that is designed for, and operated at, pressures above 45 barg. As the upper end of this pressure range is approximately equal to that of a typical hydrogen pipeline, no additional hydrogen product compression would thus be necessary.

Stream 120 is feed into shifted gas compressor 113, then into methanol reactor 110. The cooled, shifted synthesis gas typically enters the methanol synthesis loop 110 at a pressure of between about 60-120 bar. At least a portion of synthesis gas is converted to methanol in the methanol synthesis loop 110. The formed crude methanol is separated from the unreacted synthesis gas by means of a gas liquid separation device (not shown). The separated crude methanol may be sent out as a product 115 or sent to the methanol distillation 111 to make high purity methanol as a product 114. The off gas 119 from the distillation column 111 may also sent back to synthesis gas reactor 103 to be used as a fuel.

For the unreacted synthesis gas, at least a portion may be recycled back to the methanol loop, passing through methanol recycle compressor 112. Any remaining unreacted syngas may be mixed with cooled shifted synthesis gas 126 and sent to a second hydrogen separation device 130, thus producing high pressure hydrogen product stream 228 and off gas stream 218. Second hydrogen separation device may operate at a higher pressure than the first hydrogen separation device 107. Second hydrogen separation device 130 may be a pressure swing adsorption unit (PSA), or a membrane unit. The PSA off gas stream 218 may be sending to syngas generator 103 and may be used as feedstock or fuel. In one embodiment, the first hydrogen separation device 107 and the second hydrogen separation device 130 are the same unit. As the methanol synthesis process is strongly exothermic, heat must be removed. This is done by generating steam, which may be exported from the system 116, or may be used internally 123 in the methanol purification unit distillation column 111.

A portion of the high pressure hydrogen 228 may be sent back to the hydrocarbon feed stream 225 and may be used in a hydrodesulfurization (HDS) reactor (not shown) to remove sulfur from hydrocarbon feedstock if necessary.

In one embodiment, where the hydrogen 128 from the first hydrogen separation device 107 is not further compressed by a hydrogen compressor 108, the high pressure hydrogen 228 may be sent entirely to a high pressure hydrogen consumer stream 209.

In another embodiment, where the hydrogen from first hydrogen separation device 107 is compressed by means of a hydrogen compressor 108 the high pressure hydrogen from second hydrogen separation device 130 may be admixed 209a downstream of the compressor 208. Thus a higher total high pressure hydrogen stream 109 may be send to high pressure hydrogen consumers without installing additional hydrogen compressor capacity.

In another embodiment, where the hydrogen 128 from the first hydrogen separation device 107 is not further compressed by a hydrogen compressor 108 the high pressure hydrogen 228 may be mixed 209b with the hydrogen from first hydrogen separation device 107.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method for the co-production of hydrogen and crude methanol, comprising: a hydrocarbon reforming or gasification device producing a syngas stream comprising hydrogen, carbon monoxide and carbon dioxide; introducing the syngas stream to a water gas shift reaction catalyst thereby converting at least a portion of the CO and H2O contained in the syngas stream into H2 and CO2 contained in a shifted gas stream; cooling the shifted gas stream and condensing and removing the condensed fraction of H2O; then dividing the shifted syngas stream into a first stream and a second stream; introducing the first stream into a first hydrogen separation device, thereby producing a hydrogen stream, and introducing the second stream into a methanol synthesis reactor, thereby producing a crude methanol stream and a methanol synthesis off gas; introducing at least a portion of the methanol synthesis off gas into a second hydrogen separation device.

2. The method of claim 1, wherein at least a portion of the hydrogen stream is returned to the process upstream of the hydrocarbon reforming or gasification device.

3. The method of claim 1, further comprising increasing the pressure of the second stream prior to introduction into the methanol syngas reactor.

4. The method of claim 3, further comprising introducing the crude methanol stream into a methanol distillation device, thereby producing a pure methanol stream and a methanol distillation column off-gas stream.

5. The method of claim 4, wherein at least a portion of the methanol distillation column off-gas stream is returned to as fuel stream to the hydrocarbon reforming or gasification device.

6. The method of claim 1, wherein the first hydrogen separation device is a pressure swing adsorption unit.

7. The method of claim 1, wherein the first hydrogen separation device is a membrane separation unit.

8. The method of claim 1, wherein the second hydrogen separation device is a pressure swing adsorption unit.

9. The method of claim 1, wherein the second hydrogen separation device is a membrane separation unit.

10. The method of claim 1, wherein the first stream of syngas and the methanol synthesis gas off gas stream is send to the same hydrogen purification device with which can be PSA or a Membrane.

11. The method of claim 1, wherein the first hydrogen separation device and the second hydrogen separation device are not the same.

12. The method of claim 11, wherein the hydrogen is further compressed by a hydrogen compressor.

13. The method of claim 11, wherein the second hydrogen separation device operates at a higher pressure than the first hydrogen purification device.

14. The method of claim 12, wherein the second hydrogen separation device operates at a higher pressure than the first hydrogen purification device, and wherein the purified hydrogen is admixed into the hydrogen stream after the hydrogen compressor downstream the first hydrogen purification device purifying shifted syngas.

15. The method of claim 1, wherein the synthesis gas generating devise is an autothermal reformer or a partial oxidation reactor.

16. The method of claim 1, wherein the synthesis gas generation device is a steam methane reformer.

17. The method of claim 1, wherein at least a portion of methanol off gas is returned to the process upstream of the syngas generator.

18. The method of claim 1, wherein at least a portion of methanol off gas is utilized as fuel in the steam methane reformer or any other combustion system.

19. The method of claim 1, further comprising introducing the crude methanol stream into a methanol distillation device, thereby producing a pure methanol stream.

20. A method for revamping an existing hydrogen production facility into a facility co-producing hydrogen and methanol, comprising of a hydrocarbon reforming or gasification device producing a syngas stream comprising hydrogen, carbon monoxide and carbon dioxide; introducing the syngas stream to a water gas shift reaction catalyst thereby converting at least a portion of the CO and H2O contained in the syngas stream into H2 and CO2 contained in a shifted gas stream; cooling the shifted gas stream and condensing and removing the condensed fraction of H2O; then dividing the shifted syngas stream into a first stream and a second stream; introducing the first stream into an existing first hydrogen separation device, thereby producing a hydrogen stream, and introducing the second stream into a methanol synthesis reactor, thereby producing a crude methanol stream and a methanol synthesis off gas; introducing at least a portion of the methanol synthesis off gas into the existing hydrogen purification device or a newly installed separated second hydrogen separation device.

* * * * *